United States Patent [19]

Ellsworth et al.

[11] Patent Number: 4,978,858

[45] Date of Patent: Dec. 18, 1990

[54] OPTICAL WEB DETECTION AND MEASUREMENT SYSTEM ESPECIALLY ADAPTED FOR CONTROLLING REPLENISHMENT OF X-RAY FILM PROCESSING CHEMICALS

[75] Inventors: Roger D. Ellsworth; William A. Richards; James T. Samuels; James K. Bober, all of Rochester, N.Y.

[73] Assignee: Eastman Kodak Company, Rochester, N.Y.

[21] Appl. No.: 364,749

[22] Filed: Jun. 9, 1989

[51] Int. Cl.$^5$ ............................................. G01N 21/86
[52] U.S. Cl. ..................................... 250/560; 356/384
[58] Field of Search ............... 250/559, 560, 571, 561; 356/383, 384, 386, 443, 444

[56] References Cited

U.S. PATENT DOCUMENTS

| | | | |
|---|---|---|---|
| 3,472,143 | 10/1969 | Hixon et al. | 354/298 |
| 3,699,349 | 10/1972 | Paulus et al. | 250/560 |
| 4,021,832 | 5/1977 | Kirchbiel et al. | 354/298 |
| 4,057,817 | 11/1977 | Korb et al. | 354/298 |
| 4,057,818 | 11/1977 | Gaskell et al. | 250/559 |
| 4,341,453 | 7/1982 | Rubin | 250/560 |
| 4,370,558 | 1/1983 | Kinoshita et al. | 250/559 |
| 4,455,562 | 6/1984 | Dolan et al. | 346/154 |
| 4,556,305 | 12/1985 | Osegowitsch | 354/298 |
| 4,603,959 | 8/1986 | Baker | 250/571 |
| 4,683,380 | 7/1987 | Shipkowski et al. | 250/548 |
| 4,780,731 | 10/1988 | Creutzmann et al. | 346/108 |

Primary Examiner—David C. Nelms
Assistant Examiner—Stephone B. Allen
Attorney, Agent, or Firm—Martin Lukacher

[57] ABSTRACT

In order to detect the presence and make measurements of the dimensions of web which travels along a path, for example film, such as X-ray film and equipment which develops such film, a linear array of light emitting devices (e.g. LEDs) is disposed opposite to an array of corresponding photodetectors to define a gap through which the web travels. The web is scanned by sequentially applying pulses of electrical power to the emitting devices. Output signals are provided from each photodetector representing the presence of the web. In order that the brightness is sufficient to detect the presence of low density (semi-opaque) webs and to maintain uniformity of brightness of illumination from emitter to emitter, the current to the emitters is computer controlled by means of a control system which responds to the signals from the photodetectors and increments or decrements the current from an initially preset level during selected scans, for example on scans which occur every 15 seconds. The preset level is sufficient so that the photodetectors detect a substantial reduction in illumination and provide corresponding output signals even when blocked by a semi-opaque film. The width of the web may be determined by counting the number of photodetectors producing these output signals during each scan and the web area passing through the detection arrays may be determined by counting output signals representing the detection of the web. In X-ray film development when a count is registered corresponding to a predetermined area of film, the developing chemicals are replenished.

18 Claims, 8 Drawing Sheets

OPTICAL WEB DETECTION AND MEASUREMENT SYSTEM ESPECIALLY ADAPTED FOR CONTROLLING REPLENISHMENT OF X-RAY FILM PROCESSING CHEMICALS

DESCRIPTION

The present invention relates to optical web detection systems utilizing arrays of light emitting sources and photodetectors, between which a web passes, for detecting the presence and the dimensions, including area, of the web. The invention relates more particularly to a system for controlling the illumination from the light emitting sources so as to ensure that even semi-opaque (low density) webs may be detected and to ensure uniformity and amount of illumination that does not adversely affect the web, such as by fogging photo-sensitive webs.

The invention is especially suitable for use in equipment for processing (developing) radiographic film such as X-ray film by detecting the film entering the processor and measuring its area using an array of infrared light emitting diodes (LED) as the light emitting sources and infrared photodetectors as optical detectors; the film area being measured by the system and used to control the replenishment of chemicals needed to maintain proper chemical activity for processing of the film.

Web (film) detection and measurement devices using arrays of light emitting diodes and photodetectors have heretofore been used for controlling the replenishment of chemicals in film processing apparatus. Such equipment as has heretofore been available has not been completely satisfactory due to variability of the light output across the array. The brightness of light (intensity) produced by the LEDs can vary from LED to LED. LED output also decreases with age and can be affected by dirt and temperature variations. Where light pipes or fibers are used to direct beams of light from the LEDs, they tend to further increase the variability in light output as seen by the web. This problem is exacerbated by the need to detect low density webs, such as semi-opaque films. Merely increasing the output illumination is not an adequate solution since the film may be sufficiently sensitive to be affected by such intense illumination or the light may pass through the film and not be diminished sufficiently to indicate the presence of the web. Also systems using such intense illumination are undesirable since they must operate over a large dynamic range, which complicates the electronic circuitry for handling the signals from the photodetectors.

In order to solve these problems, attempts have been made to use ultrasonic technology rather than optical technology. Ultrasonic detectors are more expensive than optical detectors and tend to be unreliable even when shielded against outside noise and vibration.

Accordingly, it is the principal object of this invention to provide an improved optical web detection system utilizing arrays of electro-optic light emitters, preferably LEDs, and photodetectors between which the web to be detected passes and wherein the intensity of illumination from the emitters is controlled so as to maintain constancy in the brightness of the illumination while providing sufficient intensity to detect a wide range of webs which may vary in optical transmitivity, as for example from completely opaque to semi-opaque.

It is a further object of the invention to provide an improved web detection and measurement system which is especially suitable for accurately controlling the replenishment of chemicals in a radiographic film processor.

It is a still further object of the present invention to provide an improved web detection and measurement system which is computer controlled for uniformity of illumination and maintenance of constancy of illumination at a predetermined intensity level or range.

It is a still further object of the present invention to provide an improved optical web system using an array of light emitters and an array of corresponding photodetectors which can be initially calibrated to produce illumination of the desired intensity level from each of the emitters and to maintain the calibration over a prolonged period of time by continually recalibrating the system.

Briefly described, a system embodying the invention which provides for web detection and measurement and which is operable on semi-opaque webs, such as X-ray films, embodies an array of light emitting sources disposed in a direction which is across the web and an array of optical detectors in receptive relationship from light from the sources. The term "web" as used herein includes continuous webs as well as sheets. Computer controlled means are provided for setting the intensity of light from each of the sources to a preset level, such that the interposition of a web between any of the sources and the detectors which are in light receiving relationship therewith will reduce the intensity of light incident on the detector below a certain threshold even when the web is semi-opaque. The computer controlled means are operative during operation of the system in the absence of any web between the sources and detector arrays and is responsive to electrical signals from the detectors, for incrementally increasing and decreasing the preset levels when the level of light received by the detectors is below and above this preset level, respectively, thereby maintaining the level of illumination uniform and at the preset level. The signals obtained when a detector is blocked by the web are utilized for measurement of the width and/or area of the web and to control the replenishment of chemicals when the detection system is used in a film processor. The signal obtained when a detector is blocked is also used to incrementally increase and decrease the preset levels to prevent the LED output from fluctuating when the web is present for extended periods.

The foregoing and other objects, features and advances of the invention, as well as a presently preferred embodiment thereof, will become more apparent from a reading of the following description in connection with the accompanying drawings in which.

Figure 3:
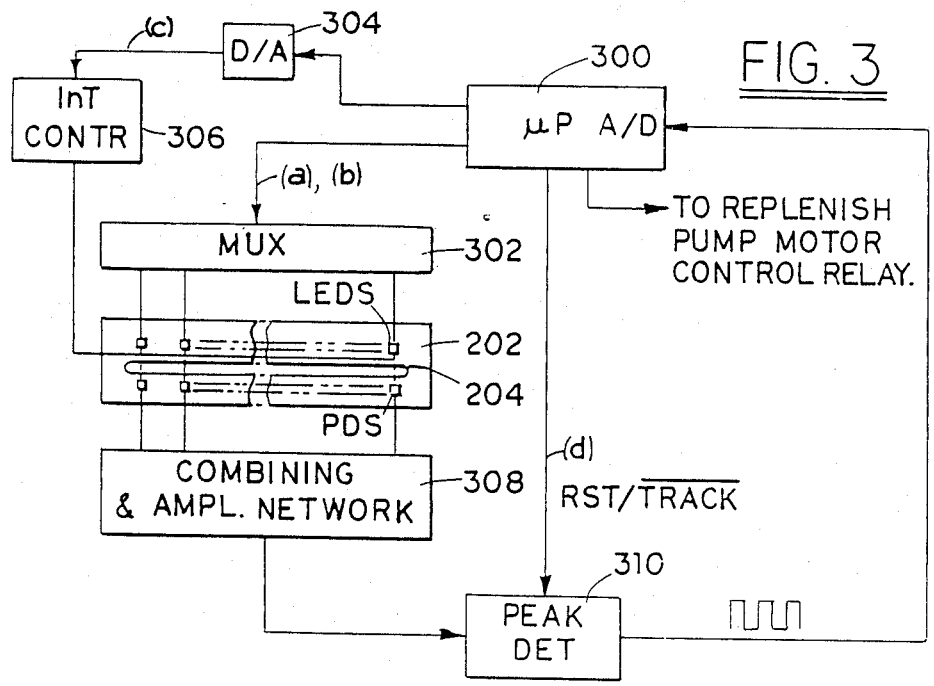
FIG. 3 is a block diagram schematically showing the film detector and measurement system which is shown in FIGS. 1 and 2.
Figure 5:
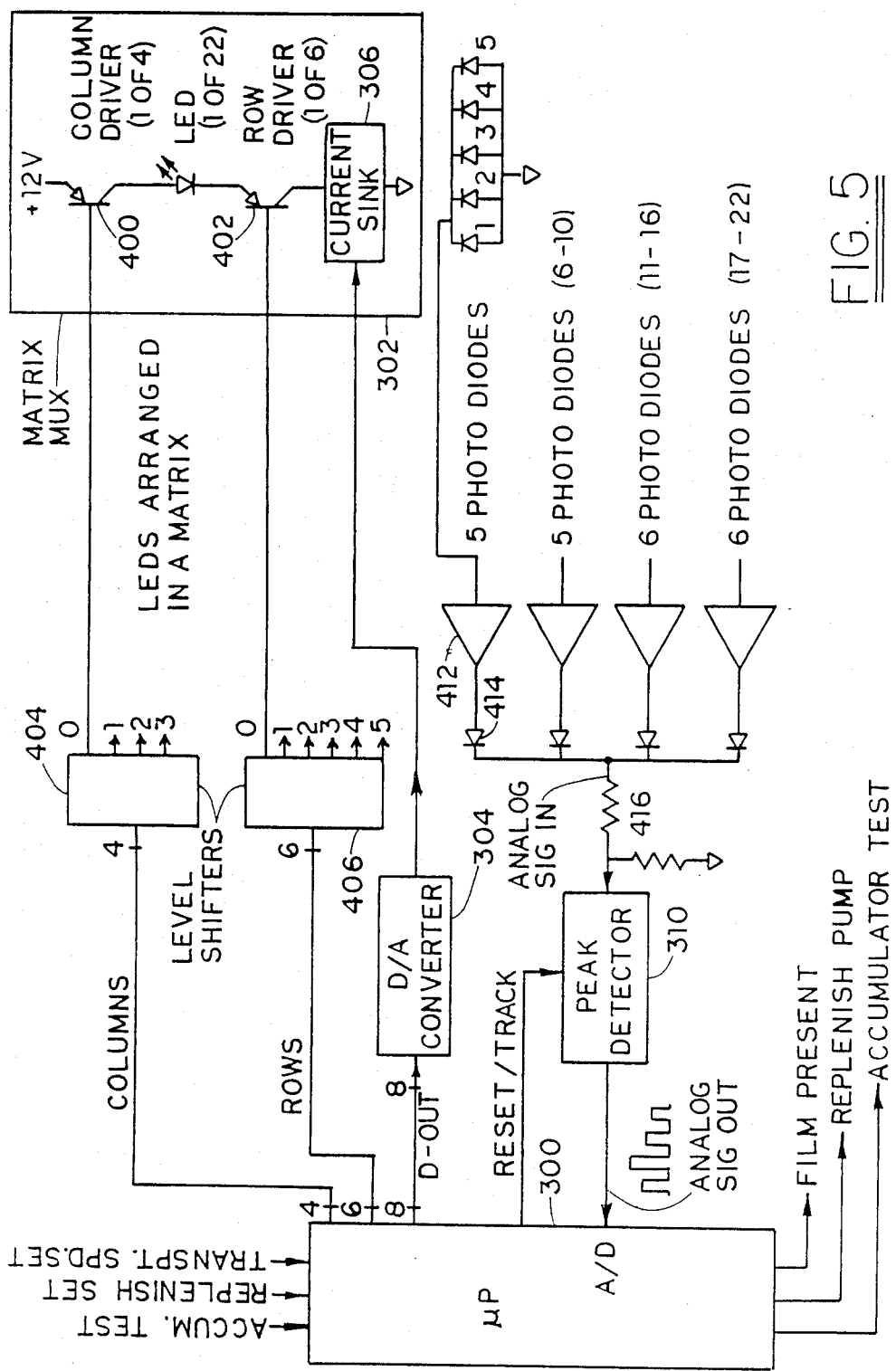
FIG. 5 is a block diagram showing the system of FIG. 3 in greater detail.
Figure 8:
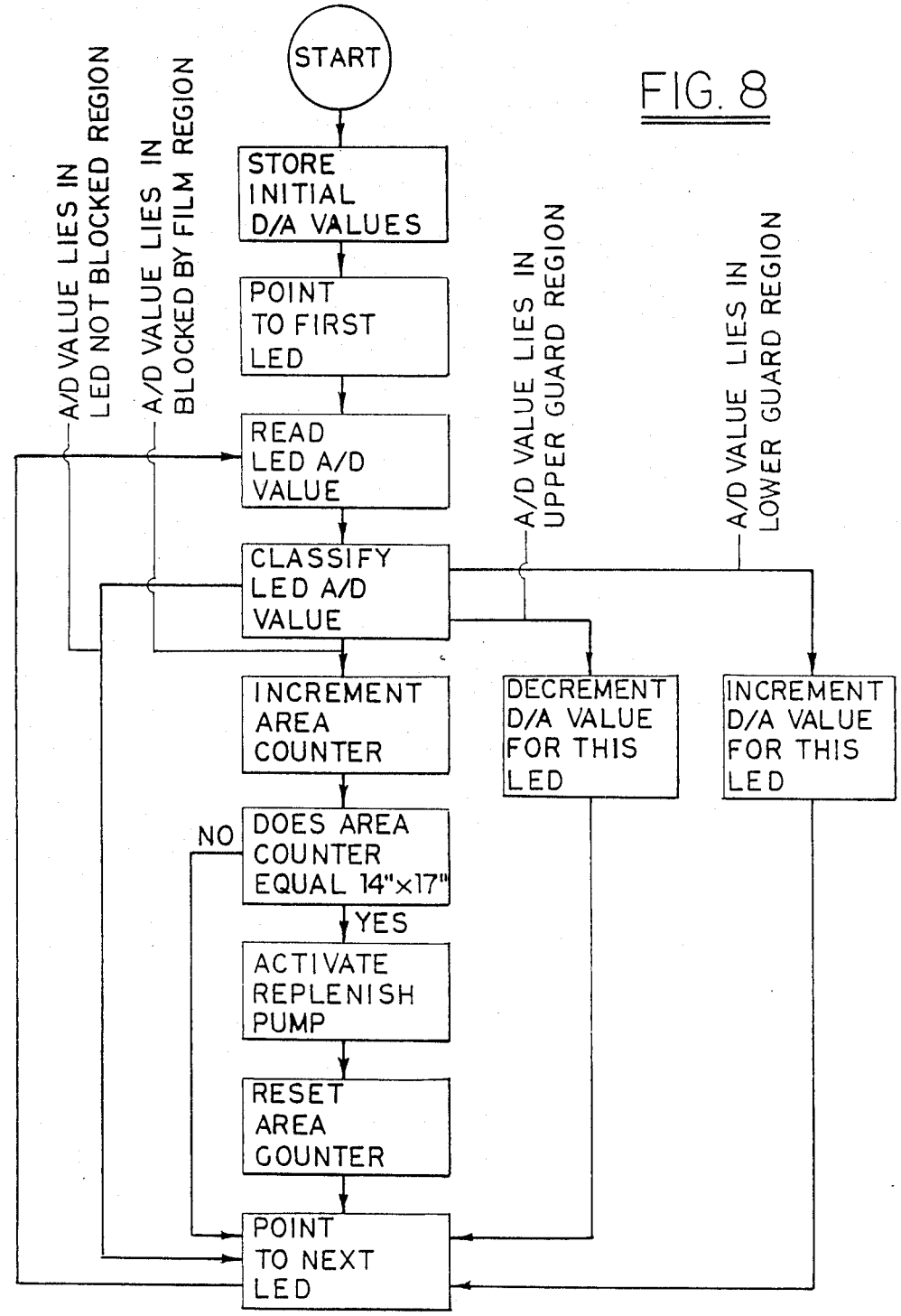
Figure 8A:
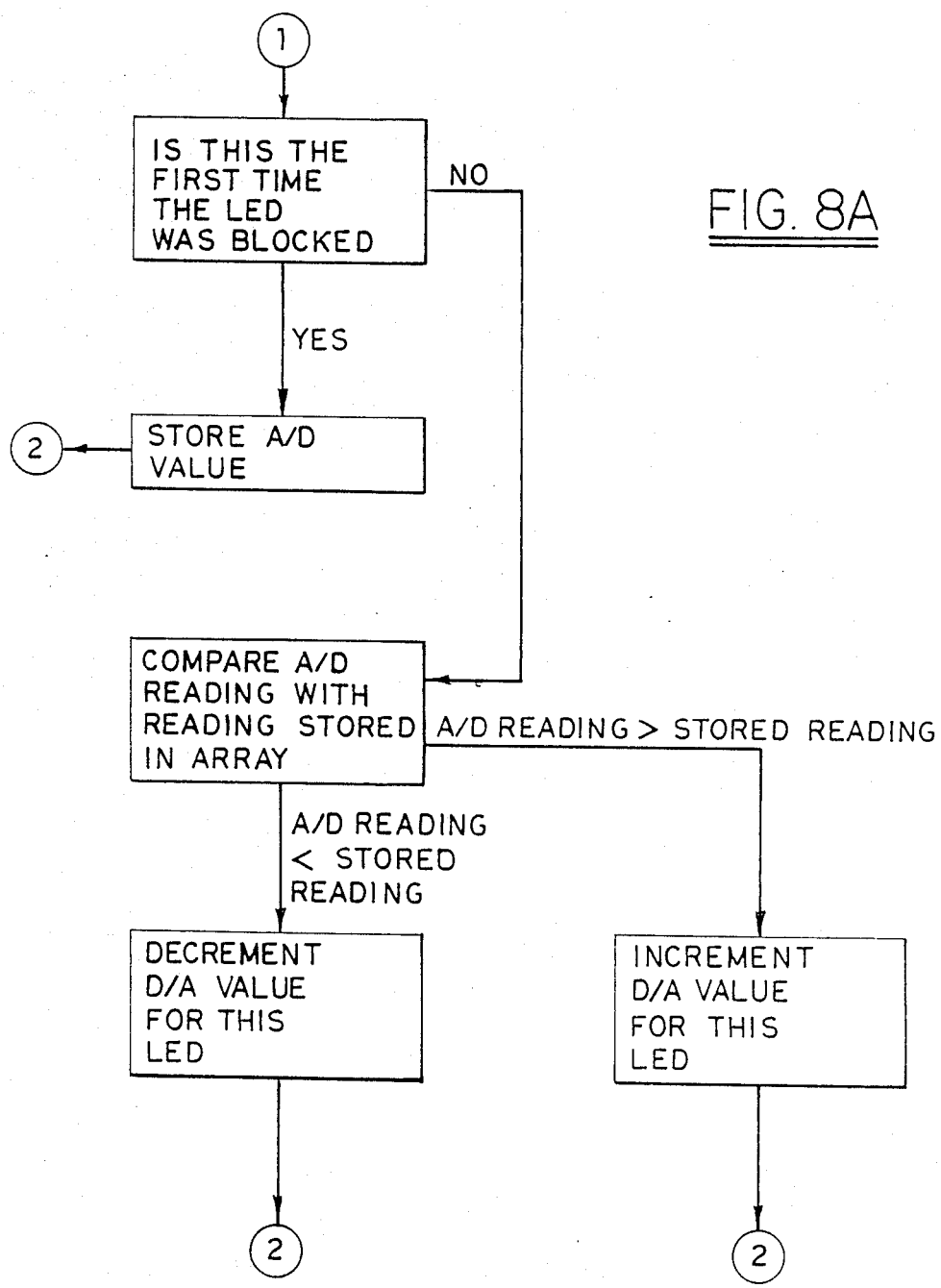
Figure 9:
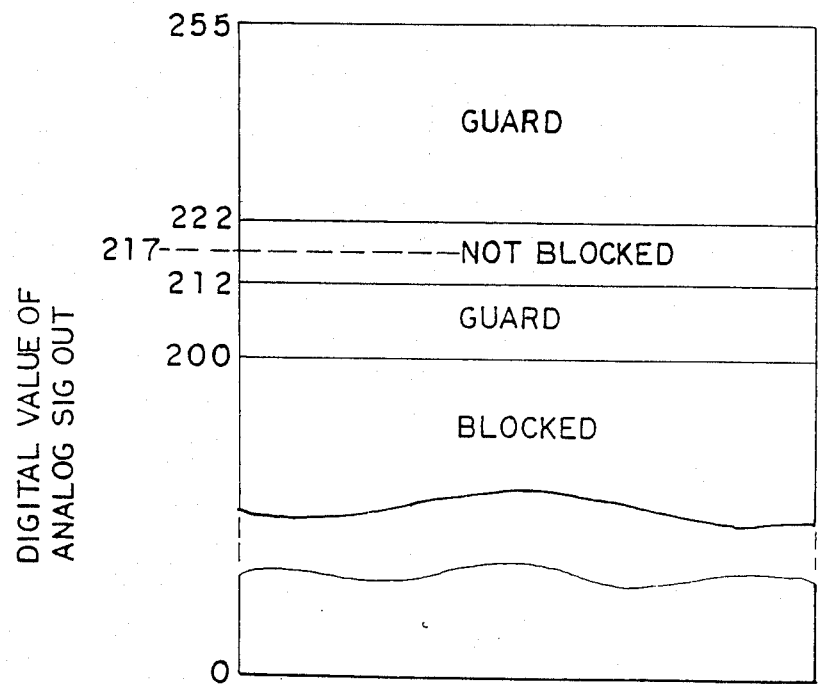

FIG. 8 and FIG. 8A constitute a flow chart illustrating the program of the computer shown in FIGS. 3 and 5; and FIG. 9 is a bar graph illustrating the digital signal values which correspond to light intensity as received by the photodetectors and measured by the peak detector shown in FIG. 5 and also in FIG. 3.

Figure 1:
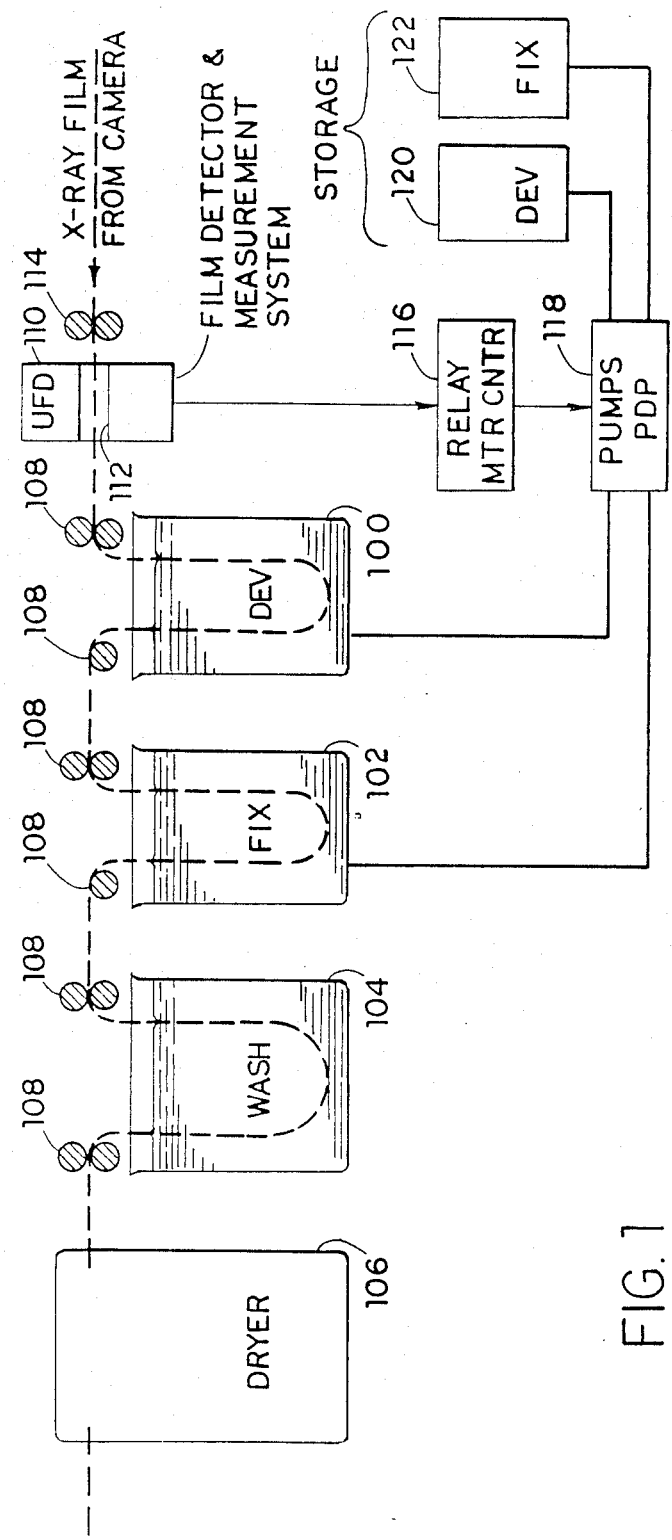
FIG. 1 is a schematic diagram of a X-ray film processing system, with film detection and measurement for chemical replenishment control, which embodies the invention.

Referring to FIG. 1, there is shown a X-ray film processor in which X-ray films, usually sheets, from an X-ray camera as used in the radiology department of a hospital or the office of a radiologist is processed. The processor has tanks 100, 102 and 104 for developing, fixing and washing of the film. After washing the film is dried in a dryer 106. Guide and drive rolls 108 which are driven by motors through suitable gearing or chain and sprocket arrangements advance the film through the tanks 100, 102 and 104 and through the dryer 106. A film detector and measurement system is disposed upstream in the direction of travel of the film from the processor tanks 100, 102 and 104 this system is referred to as a universal film detector or UFD 110. It has a gap 112 through which the film is driven at constant speed by a drive roller arrangement 114. The speed may be varied, but once set is constant. Based upon the speed of the film and the width thereof, the UFD 110 computes the area of film which has passed through it. Then it operates a motor control, such as a relay 116. The relay turns on the motor of pumps, suitably positive displacement (PDP) pumps, for an interval of time sufficient to meter enough chemicals (developer and fixer) from supply tanks 120 and 122 to replenish the chemistry in the fixer and developer tanks 100 and 102. The pumps are turned on for a fixed period of time, for example 10 seconds which will be enough to meter sufficient developer and fixer for processing a certain area of film, for example a 14×17 inch sheet of film.

Figure 2:
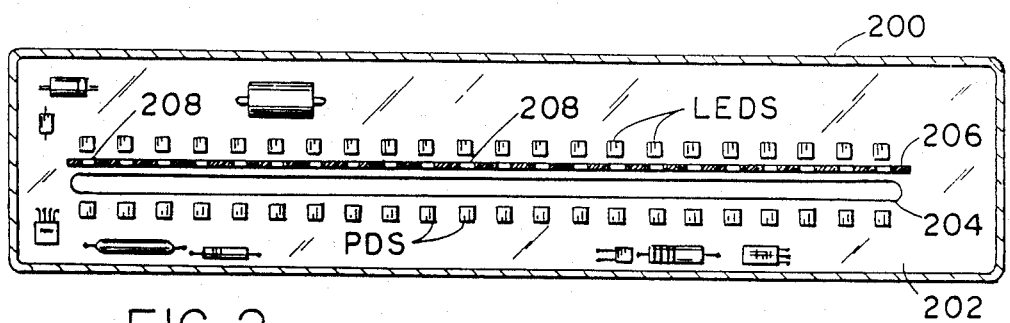
FIG. 2 is a view in elevation of the X-ray film detector and measurement system shown in FIG. 1.

Referring to FIG. 2 the UFD is illustrated. It contains a housing 200 in which is mounted a printed circuit board 202. The housing and board have aligned slots (slot 204 on the board 202 being shown in FIG. 2) through which the film passes. On the board is a linear array of infrared LEDs (e.g., twenty-two LEDs) which are equally spaced from each other along the slot 204. Opposite to the LEDs is an array of photodetectors. Twenty-two photodetectors may be used each corresponding to a different one of the LEDs and each in light receptive relationship therewith (aligned with its corresponding LED). To prevent scattering of light from the LEDs and to control the dimensions of the beam of the light from each LED, an aperture plate 206 is disposed between the LED array and the slot 204. This aperture plate has twenty-two apertures 208 each aligned with a different LED. Components such as computer chips, resistors, and capacitors of the UFD are mounted on the board 202 and connected by printed wiring (not shown) to the LEDs and photodetectors.

Referring to FIG. 3 there is shown the slot 204 and the board 202 with the aligned LEDs and photodetectors in their respective arrays. The system is controlled by a microprocessor, for example, Motorola type MC68HC11 which has a built-in analog digital converter (A/D). The microprocessor 300, via a multiplexer 302, applies sequentially to the LEDs operating currents so that they illuminate (emit light pulses) sequentially and successively scan the slot 204 and any film therein. The current through the LEDs and therefore the intensity or brightness of illumination is controlled by the microprocessor which outputs a digital value to a digital to analog converter (D/A) 304. The analog output from the D/A 304 operates an intensity control circuit 306 which is a variable amplifier or current sink described more fully in connection with FIGS. 5 and 6.

The brightness from the LEDs is made uniform from LED to LED and at a preset level. The setting of the brightness utilizes signals from the photodetectors which are combined in a combining and amplification network 308. This network provides an analog signal to a peak detector. The peak detector is enabled by the microprocessor 300 and provides output pulses corresponding in amplitude to the intensity of illumination detected by the the network 308. These pulses are outputted by the peak detector 310 to the A/D input of the microprocessor 300. The microprocessor controls or recalibrates the LEDs so as to maintain the uniform intensity of illumination in spite of aging, dirt or other other environmental effects. It also assures that the level of illumination is such that even low density or semi-opaque films in the slot 204 are detected, without using an intensity of illumination which might adversely affect (fog) the film. When the film is in the slot a series of pulses below a preset threshold are detected. These pulses are counted and used to compute the area of the film passing through the slot. The output is applied to the replenishment motor pump control 116 (FIG. 1).

Figure 4:
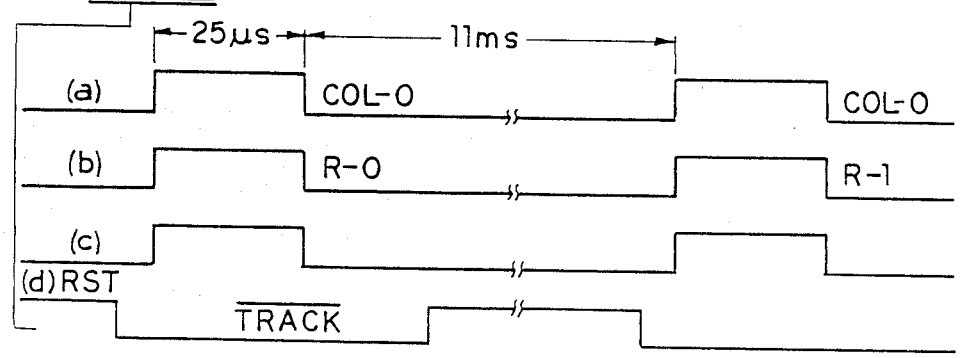
FIG. 4 is a timing diagram illustrating the operation of the system shown in FIG. 3.

The system shown in FIG. 3 operates on a sequential or serial basis to successively scan the slot. It also operates with pulses or flashes of illumination thereby further reducing the possibility of adverse affect on any film in the slot 204 by excessive illumination. As shown in FIG. 4 there are enabling pulse trains (a) and (b) which are applied to the multiplexer 302. These pulses are relatively short, for example, 25 microseconds, and are applied to successively enable the LEDs with 11 milliseconds (ms) between pulses. Pulses in train (a) are column enabling pulses while pulses in train (b) are row enabling pulses. Simultaneous occurrence of the pulses enables the multiplexer to allow passage of current through the intensity control or current sink 306 (see FIG. 5). The current level is represented by the output signals from the D/A as the pulses in train (c). Upon simultaneous occurrence of these pulses, a particular LED is turned on. After a sequence of twenty-two of these pulses (there being 22 LEDs as shown in FIG. 2) a scan is completed. It has been found that with short pulses of 25 microsecond duration with 11 milliseconds between pulses, a scan requires approximately 233 milliseconds. Scanning goes on continuously during run time, while the processor is on and ready to process film.

The microprocessor outputs the RST/$\overline{\text{TRACK}}$ control level to the peak detector 310. This level is shown in (d). Prior to the predetermined period when LED is turned on, the control signal switches from reset (RST) to track level and enables the peak detector to see and track the amplitude of the pulse. The pulse which is tracked will correspond to the LED which is illuminated. At the end of the track interval, the microprocessor reads the signal from the peak detector. Then, the RST/$\overline{\text{TRACK}}$ signal reverts to the RST level which readies the peak detector (by discharging a storage capacitor 602 (FIG. 7)) so as to be ready for the next pulse from the next photodetector.

Figure 6:
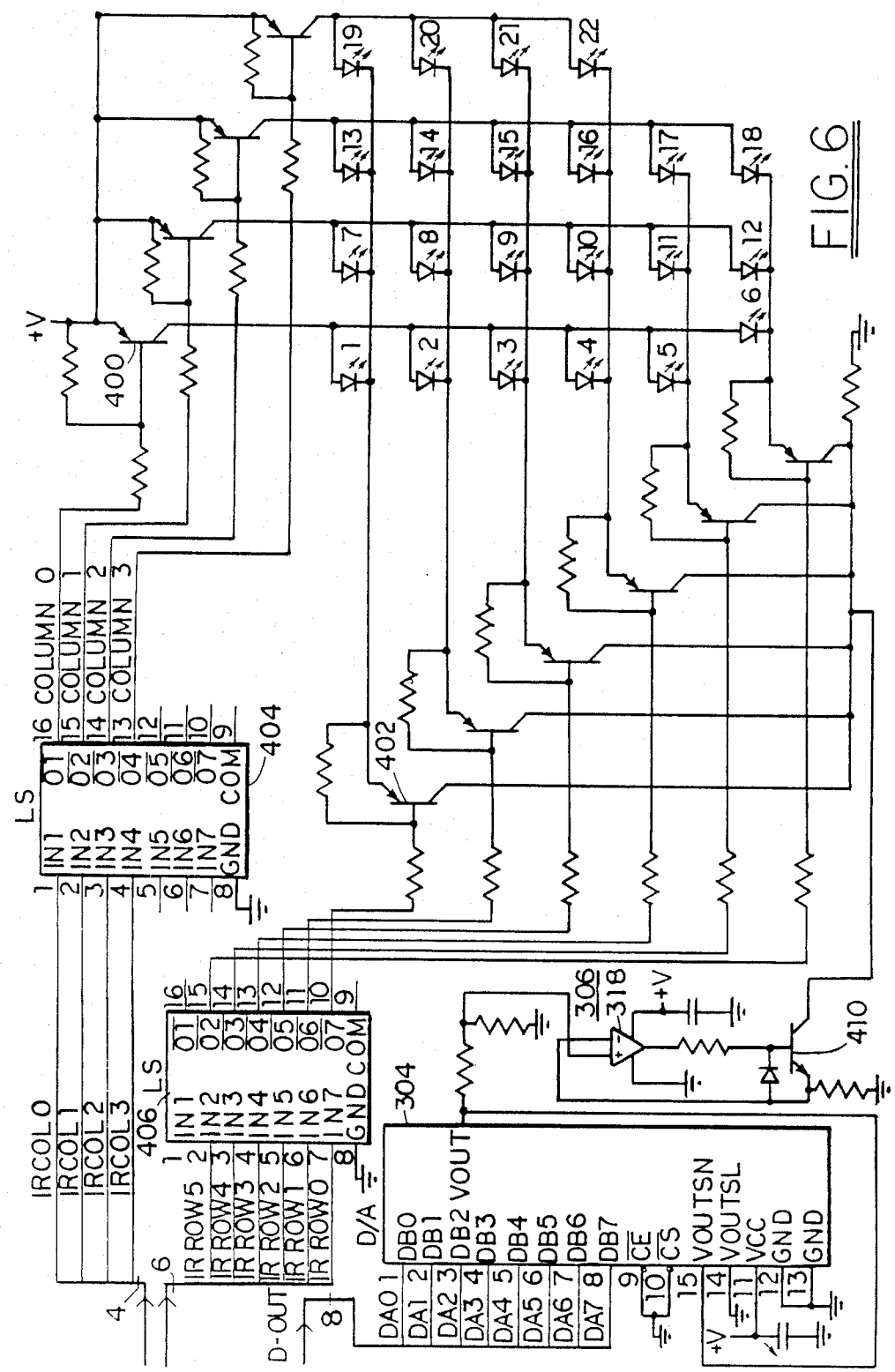
FIG. 6 is a schematic diagram of the multiplexing matrix and current control components of the system shown in FIG. 5.
Figure 7:
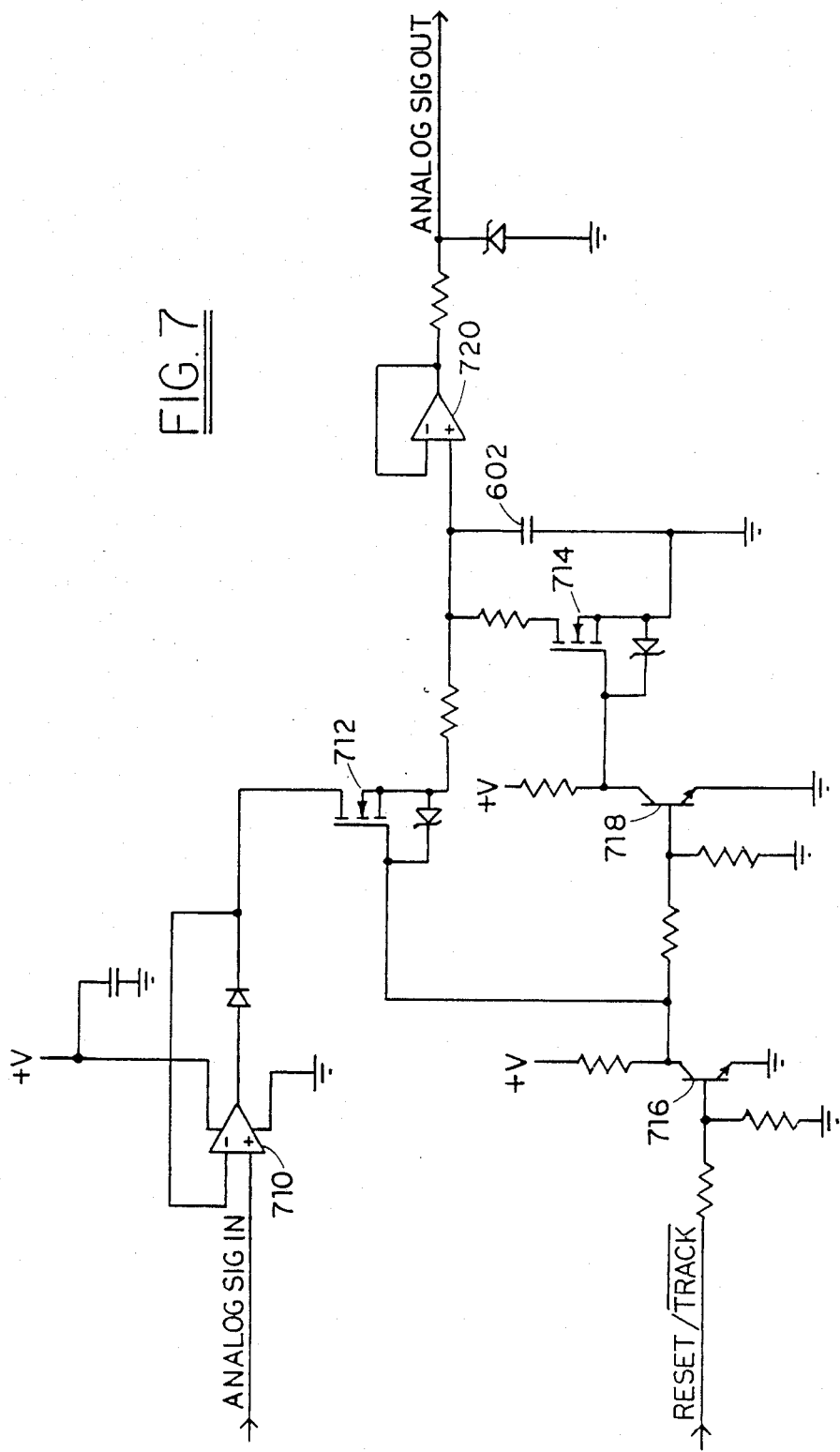
FIG. 7 is a schematic diagram of the peak detector shown in FIG. 5.

The control system will become more apparent from FIGS. 5, 6 and 7. The microprocessor has manual controls and provides outputs to a LED display (not shown) on the board 202 (FIG. 2). The controls which may be actuated by push buttons, are called the accumulator test controls. Diagnostics such as application of certain currents to the LEDs may be enabled upon accumulator test to determine if the LEDs are operating, for example, with a predetermined output level as measured by the microprocessor from the peak detector analog signal output in response to a certain current as presented to an LED via the D/A converter 304.

The replenish set, sets the time duration during which the replenish pump will be run (see FIG. 1), for example, to meter chemicals for a 14×17 inch film area. The transport speed set sets the measurement computation in accordance with the speed at which the film is driven through the processor. This speed may be varied by the processor's motor controllers, by gear changes in the film drive, or the like.

The matrix multiplexer (MUX) 302 effectively provides column and row pulses for sequentially enabling pulses of current from +12 V (the power supply) through column transistor switches 400 and row transistor switches 402. Only one of the 22 LEDs is illustrated in the multiplexer in FIG. 5. The matrix of rows and columns of the 22 LEDs is shown in FIG. 6. The first row and column transistors 400 & 402 (column 0 and row 0) are shown in FIG. 5. The microprocessor outputs digital signals which switch these transistors on and off through level shifters 404 and 406. It will be apparent that the LEDs are enabled in sequence by the four-bit and six-bit digital signals from the microprocessor 300 which are applied to the level shifters 404 and 406 to shift the voltage levels for operation of these transistors. The sequence of enablement is in the order stated, i.e., LED 1 followed by LED 2 followed by LED 3 ... through LED 22, which completes a scan and then back to LED 1 and so forth. The current path is not completed until the current sink 306 is operated. The current sink 306 is provided by an operational amplifier 318 which receives the analog signal from the D/A 304. The signal level, and therefore the current level, is determined by an 8-bit digital signal (D-out) and therefore has 256 (0 to 255) increments. The current level is therefore controllable in 256 increments in this illustrative embodiment by controlling the current through the current sink transistor 410. Upon coincidence of the enabling pulses and the application an enabling analog signal to the current sink 306, a LED (1 through 22) will be illuminated at certain level of illumination (1 of 256 levels) as determined by the D-OUT digital value.

The photodetectors are, as shown in FIG. 5, connected together in groups. Their output signals are applied through transimpedence (current to voltage conversion) amplifiers 412 which provide output voltages (an analog signal shown in FIG. 5 by the legend ANALOG SIG IN) through isolation diodes 414. The signal amplitude is controlled by a voltage divider 416 and applied to the peak detector 310.

A suitable circuit for the peak detector is shown in FIG. 7. ANALOG SIG IN is buffered in an amplifier 710 and applied to a first switch in the form of an FET 712 which is in series with the storage capacitor 602. Another FET 714 is connected and parallel with the storage capacitor 602. The RST/$\overline{TRACK}$ control signal is applied to the series FET switch 712 through a transistor driver 716, and to the parallel FET 714 through an inverting transistor 718. Accordingly, during the reset time the peak detector is reset by discharge of the capacitor 602. During track time the ANALOG SIG IN is applied through the FET 712 to the storage capacitor 602 and the peak level thereof is detected. The output signal (ANALOG SIG IN) is derived from a buffer amplifier 720 and applied to the A/D input of the microprocessor 300.

The operation of the system will become more apparent from FIGS. 8, 8A and 9. On start-up initial D/A values (the values of the D-OUT signal) which will obtain a certain level of intensity from each of the 22 LEDs is stored in the memory of the computer. This D-OUT value may vary from LED to LED. For example, it may correspond to 45 for the first LED, 30 for the second LED, 60 for the third LED, out of a scale of 0 to 255; 255 being the maximum output. The uniformity of intensity is measured by way of ANALOG SIG OUT. The values of the corresponding 8-bit binary signal digitized by the A/D input of the microprocessor 300, is shown in FIG. 9. The selected value, for example, is 217. This is in a range from 212 to 222 and is desirably in the center of the range. The level of intensity is such that the least dense or most transparent (semi-opaque) film when present will produce an ANALOG SIG OUT which in digital value is in the blocked range of from 0 to 200 and preferably in the middle of that range, approximately 100.

Also as shown in FIG. 9, there are guard ranges above and below the predetermined level of 217. The lower guard range is from 200 to 212 while the upper guard range is from 222 to 255.

Referring again to FIG. 8, after initialization and the storage of the initial values in the memory of the microprocessor, the system is ready to run. Now the microprocessor points to and enables the first LED. The ANALOG SIG OUT is read by the computer. The computer classifies this output in accordance with its value as to whether or not the value lies in the blocked region (0-200). Then a counter in the microprocessor is incremented. This is an area counter. Depending upon the transport speed which was set into the computer, a certain count is detected which corresponds to a certain area of film, in this embodiment the area is 14×17 inches. In other words, an area of film is measured depending upon the number of LEDs blocked by the film region in the slot 204 (FIGS. 2 and 3). If the count is equal to or greater than that corresponding to the 14×17 inch sheet, the motor control is activated and the replenish pump is turned on for a predetermined period of time. Then the area counter is reset. After this computation the system points to the next LED.

Every 20 scans, or approximately every 15 seconds for the sampling and scanning times illustrated in FIG. 4, a recalibration program is executed which classifies the ANALOG SIG OUT value in terms of its corresponding A/D value from 0 to 255. If film is interposed between the LED and photodiode, the A/D value is compared to the first reading that indicated film was present. If the A/D value is greater than the stored reading then the D to A value which was stored in the microprocessor memory is decremented by one (1 out of 256 on an 8-bit binary scale). If the A/D value is less than the stored reading then the D to A will be incremented by one. When film is not present A/D values for each LED during a scan is classified as to whether no value lies in the not blocked region (corresponding to 212 to 222)—see FIG. 9) or in the upper or lower guard regions. If in the upper guard region, the illumination is too intense. Then the D to A value which was stored in the microprocessor memory is decremented by one (1 out of 256 on an 8-bit binary scale). If the value is detected to be in the lower guard region (from 200 to 212) the intensity is too low and the stored D to A value for the LED which is enabled is incremented by one. The successive incrementing and decrementing of the stored values recalibrates the system so that the intensity of illumination remains uniform and substantially constant during the run mode. Such constant illumination at the requisite level assures detection even of semi-opaque film.

From the foregoing description it will be apparent that there has been provided an improved web detection and measurement system. Variations and modifications of the herein described system and the scope of the invention will undoubtedly suggest themselves to those skilled in the art. Accordingly, the foregoing description should be taken as illustrative and not in a limiting sense.

We claim:

1. A system which provides for web detection and measurement and which is operable on semi-opaque webs such as x-ray films, which system comprises an array of light-emitting sources disposed in a direction which is across the web, an array of optical detectors in receptive relationship for light from said array of sources, means for presetting the intensity of light from each of said sources to a first level such that the interposition of a web between any of said sources and the detectors in light receiving relationship therewith will reduce the intensity of light incident on that detector below a certain threshold even when said web is semi-opaque, and means operative during web detection operation of said system and responsive to signals from said detectors for incrementally increasing and decreasing said pre-set levels when the level of light received by said detectors is respectively below and above said first level so as to maintain said first level of intensity.

2. The system according to claim 1 wherein said means for incrementally decreasing said intensity includes means responsive to said signals when they correspond to a first range of intensity above said first level for decreasing said level by a certain increment of intensity corresponding to less than 1% of the variation in amplitude of said signals between the amplitude when said detectors are not illuminated and when illuminated at the upper end of said first range.

3. The system according to claim 2 wherein said means for incrementally varying said intensity includes means responsive to said signals when they correspond to a second range of intensity below said first level or increasing said first level by said certain increment.

4. The system according to claim 3 wherein said first and second ranges are spaced from each other by a given range of intensity which includes said first level approximately at the center thereof.

5. The system according to claim 4 further comprising means operative to detect the interposition of a web between said array of sources and said array of detectors when said detectors provide signals corresponding to light intensity below said second range.

6. The system according to claim 1 further comprising means responsive to said signals corresponding to intensity of illumination of said detectors at a level below said certain threshold for measuring the area of said web.

7. The system according to claim 6 further comprising means for chemically processing said web disposed downstream of the direction of travel of said web from said arrays, and means for supplying fresh chemicals to said processing means when a predetermined area of said web is measured.

8. The system according to claim 1 further comprising a housing having a slot therethrough for the passage of said web, at least one circuit board mounted on said housing with portions on opposite sides of said slot, said detector array and said source array each being a linear array of spaced devices disposed on said board on opposite sides of said slot, said source devices and detector devices being in alignment so that a different one of said source devices is opposite to a different one of said detector devices, an aperture plate disposed on one of said opposite sides adjacent to said source devices, said aperture plate having a plurality of apertures each aligned with a different one of said source devices.

9. The system according to claim 8 wherein said source devices are light emitting diodes (LEDs) and said detector devices are photodiodes.

10. The system according to claim 1 wherein each of said light emitting sources corresponds to a different one of said optical detectors and the emitted light is of intensity corresponding to current therethrough, a computer, means controlled by said computer for enabling the passage of predetermined current levels through successive ones of said sources in said array for predetermined periods of time, thereby scanning across said web, said computer and control means providing said presetting means, means controlled by said computer for sampling said optical detectors during each of said predetermined periods of time for providing said signals from successive ones of said detectors, and said computer including means for incrementally increasing and decreasing the current to said sources for maintaining said first level of intensity.

11. The system according to claim 10 wherein said computer controlled means comprises means connected in common to all of said sources and responsive to digital signals provided by said computer for controlling said current during said predetermined periods, and multiplexing means connected to said computer for successively enabling the passage of such current through said light emitting sources.

12. The system according to claim 10 wherein said light emitting sources are photodiodes arranged in a matrix of rows and columns and said multiplexing means comprises switching means comprised of said rows and columns of diodes for enabling the passage of said current through successives ones of said diodes and then through said common current control means.

13. The system according to claim 12 wherein said computer controlled sampling means comprises a peak detector connected in common to all of said photodiodes, means operated by said computer for operating said peak detector to sample said signals during said predetermined periods, and means included in said computer for digitizing said samples of said signals.

14. The system according to claim 13 wherein said sampling means comprises first and second switches, a capacitor connected in series with said first switch, and in parallel with said second switch, means for closing said first switch and opening said second switch immediately prior to each of said predetermined period of time for closing said second switch and opening said first switch between each of the predetermined periods whereby to discharge such capacitor and enable peak detection of the signal from the next successive photodiode.

15. The system according to claim 1 further comprising means for successively illuminating said light emitting sources in said array for scanning said web, and means for operating said incrementing and decrementing means every Nth scan where N is of the order of 10.

16. The system according to claim 1 wherein said means for increasing and decreasing is operative includes means operative in the absence of any web between the source and detector arrays.

17. The system according to claim 1 wherein said means for increasing and decreasing is also operative when web is present between the source and detector array.

18. The system according to claim 10 further comprising means for operating said sources to provide light as trains of pulses of light.

* * * * *